(12) United States Patent
Jarzynski et al.

(10) Patent No.: US 6,360,610 B1
(45) Date of Patent: Mar. 26, 2002

(54) CONDITION MONITORING SYSTEM AND METHOD FOR AN INTERFACE

(76) Inventors: Jacek Jarzynski, 1146 Roxboro Dr., Atlanta, GA (US) 30324; Richard Frank Salant, 1138 Manning Farms Ct., Dunwoody, GA (US) 30338; William B. Anderson, 605 Creekwood Crossing, Roswell, GA (US) 30076

(*) Notice: Subject to any disclaimer, the term of this patent is extended or adjusted under 35 U.S.C. 154(b) by 0 days.

(21) Appl. No.: 09/702,299

(22) Filed: Oct. 31, 2000

Related U.S. Application Data
(60) Provisional application No. 60/162,940, filed on Nov. 2, 1999.

(51) Int. Cl.[7] .......................... G01N 29/00; G01N 11/00
(52) U.S. Cl. ...................... 73/627; 73/32 A; 73/54.41; 73/629
(58) Field of Search .................. 73/627, 629, 597, 73/599, 579, 1.82, 61.79, 630, 632, 290, 54.41, 54.42, 32 A

(56) References Cited

U.S. PATENT DOCUMENTS

| | | | | |
|---|---|---|---|---|
| 4,779,452 A | * | 10/1988 | Cohen-Tenoudji et al. | 73/54.41 |
| 5,095,754 A | * | 3/1992 | Hsu et al. | 73/602 |
| 5,269,189 A | * | 12/1993 | Thompson et al. | 73/632 |
| 5,365,778 A | * | 11/1994 | Sheen et al. | 73/54.41 |
| 5,433,112 A | * | 7/1995 | Piche et al. | 73/597 |
| 5,439,157 A | * | 8/1995 | Geier et al. | 73/643 |
| 5,929,336 A | * | 7/1999 | Belanger et al. | 73/622 |
| 6,003,872 A | | 12/1999 | Nord | 277/317 |
| 6,019,000 A | * | 2/2000 | Stanke et al. | 73/622 |
| 6,065,345 A | | 5/2000 | Holenstein et al. | 73/660 |
| 6,079,273 A | * | 6/2000 | Latimer et al. | 73/622 |
| 6,164,136 A | * | 12/2000 | Hirsekorn et al. | 73/602 |

OTHER PUBLICATIONS

"Detection of Lubricating Film Breakdown In Mechanical Seals," William B. Anderson, Richard F. Salant, and Jacek Jarzynski, TRIB–vol. 7, Emerging Technologies for Machinery Health Monitoring and Prognosis, ASME 1997.

"Ultrasonic Detection of Lubricating Film Collapse in Mechanical Seal,©" William Anderson, Richard F. Salant and Jacek Jarzynski, vol. 42 (1999), 4, 801–806, Tribology Transactions.

"Condition monitoring of mechanical seals using actively generated ultrasonic waves," R.F. Salant, W. Anderson, and J. Jarzynski, George W. Woodruff School of Mechanical Engineering, Georgia Institute of Technology, GA.

* cited by examiner

Primary Examiner—Hezron Williams
Assistant Examiner—Jacques Saint-Surin
(74) Attorney, Agent, or Firm—Thomas, Kayden, Horstemeyer & Risley

(57) ABSTRACT

A system and a method are provided for monitoring the condition of an interface. Although not limited to this particular application, the system and method are particularly suited for monitoring the interface of two liquid lubricated mechanical seal faces. The system monitors an interface by using a wave source to produce an ultrasonic shear wave, directing the wave at the interface, detecting the wave after it interacts with the interface, and comparing the detected wave to predetermined wave characteristics. Based on the comparison, an alarm may be triggered. The alarm may indicate that the mechanical seal is failing.

52 Claims, 3 Drawing Sheets

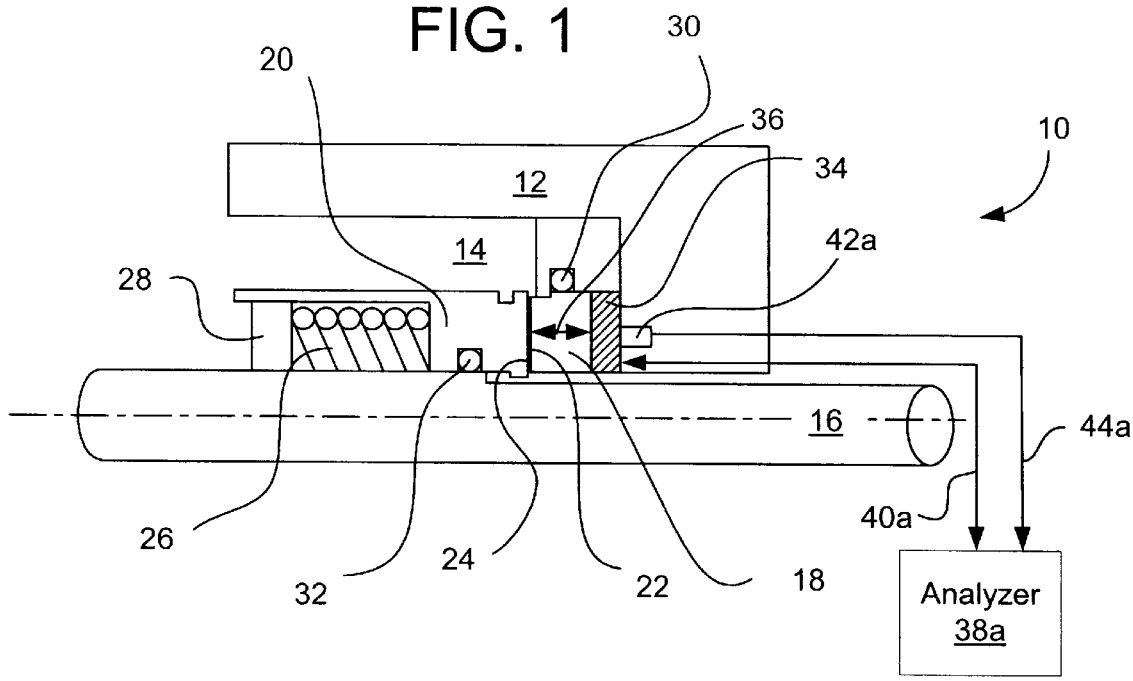
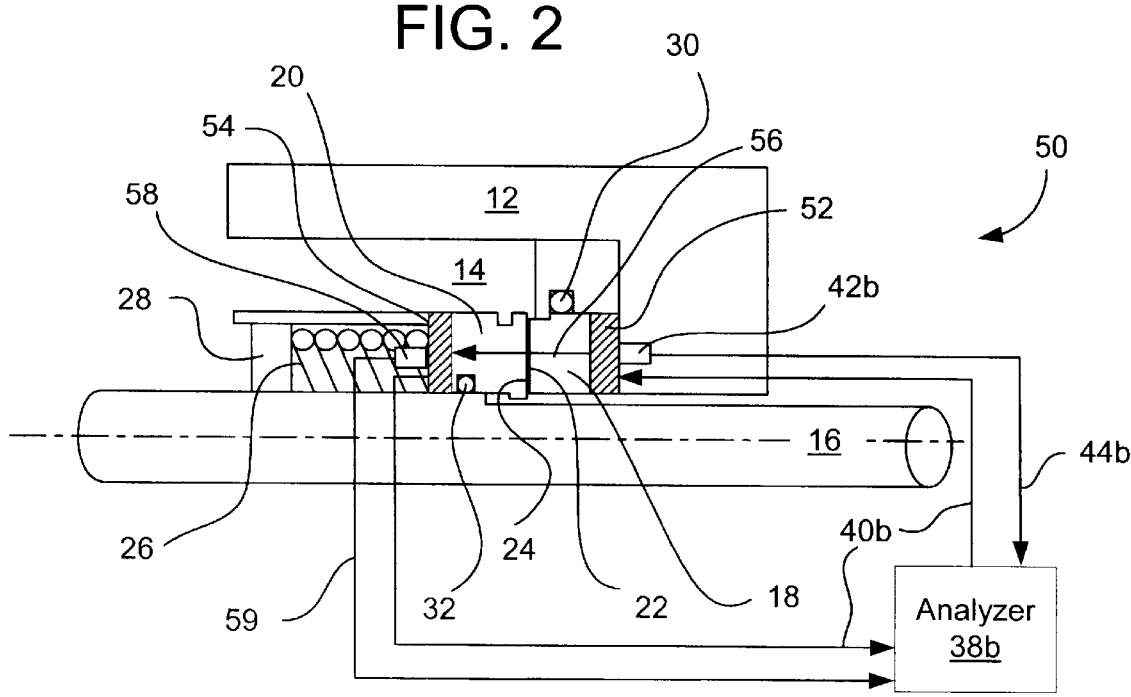

CONDITION MONITORING SYSTEM AND METHOD FOR AN INTERFACE

CROSS-REFERENCE TO RELATED APPLICATION

This application claims priority to copending U. S. provisional application entitled, "CONDITION MONITOR FOR A LIQUID MECHANICAL SEAL," having Ser. No. 60/162, 940, filed Nov. 2, 1999, Georgia Tech Docket No. 2137PR, which is entirely incorporated herein by reference.

STATEMENT REGARDING FEDERALLY SPONSORED RESEARCH OR DEVELOPMENT

The U.S. government may have a paid-up license in this invention and the right in limited circumstances to require the patent owner to license others on reasonable terms as provided for by the terms of GIT Project No. E-25-T-46 awarded by the U.S. Office of Naval Research under research grant N00014-95-1-0539, entitled Integrated Diagnostics.

TECHNICAL FIELD

The present invention is generally related to methods and equipment for monitoring the interface of two surfaces and, more particularly, is related to a system and method for monitoring the interface of two liquid lubricated mechanical seal faces.

BACKGROUND OF THE INVENTION

Although not limited to any particular interface, the background of the condition monitor is provided with reference to the interface between the two faces of liquid lubricated mechanical seals.

Condition monitoring of liquid lubricated mechanical seals is based on the observation that the proximate cause of most seal failures is excessive contact between the faces. Such contact leads to mechanical and thermal damage to the faces, and ultimately, to seal failure. Thus, excessive face contact is a precursor to seal failure. Therefore, the detection of contact and measurement of the severity of contact would allow preventive action to be taken to avoid seal failure.

The most extensively investigated approach to condition monitoring of liquid lubricated mechanical seals is the acoustic emission (AE) method. AE relies on the emission of ultrasonic acoustic waves by a pair of surfaces when they are in sliding contact. This approach has not proven to be commercially feasible for a variety of reasons. First, it is very difficult to distinguish seal emissions from the emissions generated by other sources (noise). Second, the seal emissions characteristics are not known a priori, so that one does not know what frequencies to listen for without first testing a particular seal. Third, seal emissions characteristics can differ from seal to seal. Fourth, even with the same seal, the emissions characteristics can change with a change in operating conditions. And fifth, with the same seal the emission characteristics can change with time as the face surfaces change (e.g. , due to wear). Thus, even if the seal emissions can be isolated and identified, their interpretation is extremely difficult.

Attempts have also been made to use alternate techniques. In one such technique, emitted audible acoustic waves are monitored instead of the ultrasonic waves, described above. Four microphones (placed outside the subject machine) are used in conjunction with a sophisticated signal-processing scheme to isolate the seal emissions from noise. The placement requirements of multiple microphones may make this approach impractical in an industrial environment. In addition, this method still suffers from the other drawbacks of the classic AE method.

Another approach involves the use of multiple conventional eddy current proximity probes to monitor the shape and power spectrum of the orbit plot of the rotating face angular misalignment. This technique can indicate whether or not contact occurs, but it has not been shown to indicate the severity of contact.

Finally, attempts have been made to use multiple conventional sensors to monitor such operating characteristics as sealed pressure, sealed temperature, housing vibration and motor current. The data from these sensors are fed into an elaborate data processing system (e.g., containing a neural network) to determine if a seal is in danger of failing. This complexity of this technique limits its application.

The benefits of condition monitoring include the reduction in the probability of catastrophic failure, the reduction or elimination of scheduled maintenance, and an increased machine or component life. The application of such condition monitoring to liquid lubricated mechanical seals has been prevented by the lack of a proven commercially available seal monitor. Although attempts have been made to develop such a monitor, none have proven successful.

Thus, a heretofore unaddressed need exists in the industry to address the aforementioned deficiencies and inadequacies.

SUMMARY OF THE INVENTION

The present invention provides a system and a method for monitoring the condition of an interface. Although not limited to this particular application, the invention provides a system and method for monitoring the interface of two liquid lubricated mechanical seal faces.

Briefly described, in architecture, the system for monitoring an interface can be implemented as follows. A wave source produces a shear wave (transverse wave). The shear wave is directed at the interface. A wave sensor detects the wave after it interacts with the interface. A wave analyzer compares the detected shear wave to predetermined wave characteristics. The system produces an output containing information regarding the comparison.

The present invention can also be viewed as providing a method for monitoring an interface. In this regard, the method can be broadly summarized by the following steps: producing a shear wave; directing the wave at the interface; detecting the shear wave after the shear wave interacts with the interface; analyzing the detected wave in comparison to predetermined wave characteristics; and producing an output containing information regarding the comparison.

In the preferred embodiment, which is meant as a non-limiting example, the approach involves detecting the collapse of the lubricating film between the seal faces and detecting excessive asperity contact. The collapse of the lubricating film and excessive asperity contact are precursors to seal failure. An ultrasonic transducer is placed behind one of the seal faces and used to produce ultrasonic shear waves (at a known frequency and amplitude) which propagate toward the interface between the two seal faces. By monitoring the amplitudes of the waves transmitted through or reflected by the interface, one can detect film collapse and the degree of contact between the faces.

This approach avoids the difficulties of the acoustic emissions method and the other methods described above.

Actively generated ultrasonic shear waves are used to diagnose the condition of the sealing interface, indicating the occurrence and severity of contact. This method uses very simple hardware and signal processing software, making it especially suitable for commercial use.

Some systems, methods, features, and advantages of the present invention have been described in the following publications which are entirely incorporated herein by reference: Anderson, W. B. , Salant, R. F. , and Jarzynski, J. , "Ultrasonic Detection of Lubricating Film Collapse in Mechanical Seals, " STLE Tribology Trans, Vol. 42, pp. 801–806, (1999); and Salant, R. F. , Anderson, W. , and Jarzynski, J. "Condition Monitoring of Mechanical Seals Using Actively Generated Ultrasonic Waves, " BHR Group Fluid Sealing, pp. 271–289 (2000).

Other systems, methods, features, and advantages of the present invention will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views. In accordance with the invention, the following figures are provided.

FIG. 1 is a cut-away view of a machine housing and a single transducer for monitoring the interface of two seal faces in a first type of mechanical seal and a block diagram showing an analyzer.

FIG. 2 is a cut-away view of machine housing, a first transducer for producing a shear wave, and a second transducer for detecting the shear wave after the shear wave interacts with the interface of the mechanical seal of FIG. 1 and a block diagram showing an analyzer.

DETAILED DESCRIPTION OF THE PREFERRED EMBODIMENT

Figure 3:
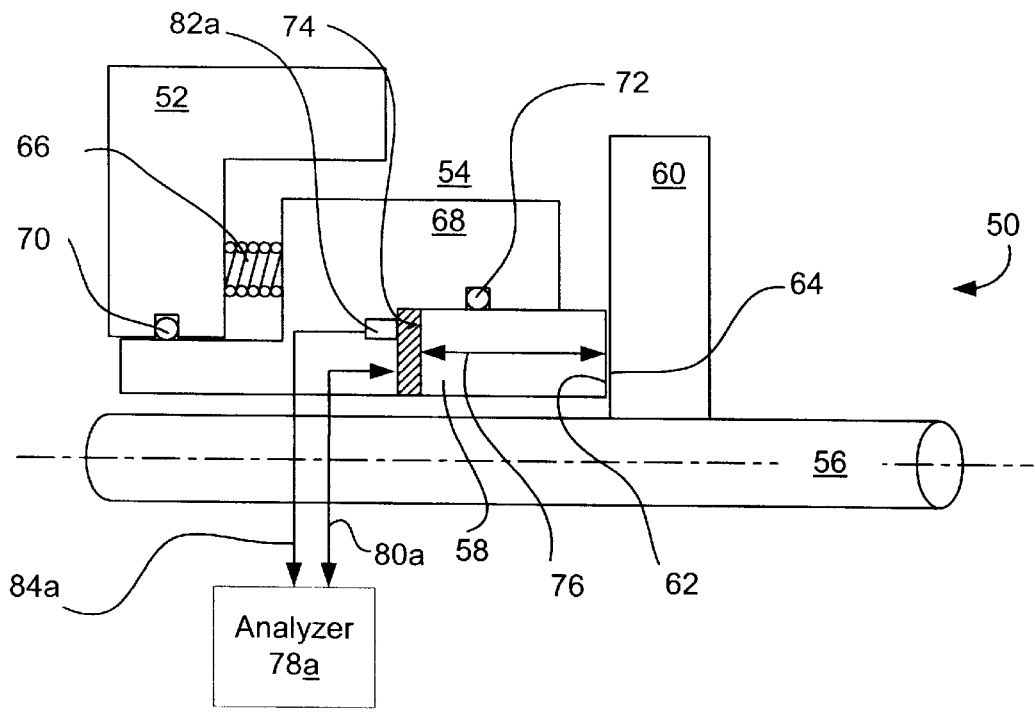
FIG. 3 is a cut-away view of a machine housing and a single transducer for monitoring the interface of two seal faces in a second type of mechanical seal and a block diagram showing an analyzer.

The condition monitor for an interface, and associated method(s), will be specifically described in the context of preferred embodiments for liquid lubricated mechanical seals. The embodiments are nonlimiting examples of implementations for the condition monitor for an interface. Numerous other embodiments are envisioned and are possible such as journal bearings and static joints. Other embodiments will be apparent to those with skill in the art. In general, the particular embodiment will be determined by the interface to be monitored.

A piezoelectric transducer is placed behind a non-rotating seal face and used as a source to produce ultrasonic shear waves at a known frequency and amplitude. Those waves propagate toward an interface between the non-rotating seal face and a rotating seal face. If there is no contact between the faces, most of the ultrasonic energy is reflected at the interface; very little is transmitted across the interface. Conversely, if there is mechanical contact between the faces, less ultrasonic energy is reflected at the interface and more is transmitted. As the contact becomes more severe, asperities are increasingly compressed and deformed, and the real area of contact increases. Consequently, the amplitudes of the reflected waves are decreased, and those of the transmitted waves, increased. Therefore, either the transmitted or the reflected wave amplitudes can be measured to determine if contact occurs and the severity of contact.

For dual seals with a single rotating face between two non-rotating faces, it is convenient to measure the transmitted waves. However, for most applications involving single, double or tandem seals, the transmitted wave technique would be difficult to implement because two transducers are required for each seal, one source and one receiver. One of those transducers would have to be mounted behind the rotating seal face and some method must be used to transmit a signal between that transducer and ground (e.g. slip rings or telemetry). Therefore, for most applications the reflected wave technique is more practical, since both the source and the receiver can be mounted behind the non-rotating face.

The condition monitor for an interface offers important advantages over the previous methods described above. Since the ultrasonic shear waves are actively generated, their frequency and amplitude can be chosen such that they can be easily distinguished from emissions generated by other sources (noise). Further, since the frequency is chosen, one knows what to listen for, and therefore an optimum transducer for the receiver can be selected and a very simple signal-processing scheme can be used. One form of a signal processing scheme is to store the reflected wave characteristics of the mechanical seal during normal operation and compare the stored wave characteristics to operating wave characteristics. The output would then be the triggering of an alarm when significant differences are noted between the stored wave characteristic and the operating wave characteristics.

A second form of a signal processing scheme is to store several reflected wave characteristics of the mechanical seal during normal operations over a period of time and compare the stored wave characteristics to operating wave characteristics and produce an output indicating the wear on the seal. The output could then be used to more efficiently maintain the seal.

Ultrasonic shear waves (transverse waves) are particularly well suited for monitoring liquid lubricated mechanical seals because the mismatch between acoustic impedances of the sealed liquid and the seal face materials is low. In shear waves, either particles of the medium in which the waves travel vibrate at right angles to the direction of the wave propagation (e.g. sonic transverse waves) or energy fields oscillate at right angles to the direction of propagation (e.g. electromagnetic waves).

Although transducers producing shear waves are particularly well suited for liquid seals, gas seals ("dry gas seals") have become increasingly popular over the last few years, especially for sealing compressors. Gas seals are particularly vulnerable to face damage caused by excessive contact and therefore would also benefit from a condition monitoring system that may use transducers producing shear waves.

FIG. 1 shows a cut-away view of a machine housing and a single transducer for monitoring the interface of two seals in a first type of mechanical seal. The machine housing and condition monitoring system as a whole is shown by reference numeral 10. In detail, FIG. 1 shows a machine housing 12. A seal chamber 14 is located in the machine housing 12. The seal chamber 14 contains a fluid. A shaft 16 is also shown.

Around the shaft 16, and within the machine housing 12, is an annular fixed portion 18 of the mechanical seal. Also around the shaft 16, and within the machine housing 12, is an annular rotating portion 20 of the mechanical seal. The annular fixed portion 18 includes a front with a fixed face 22. The annular rotating portion 20 includes a front with a rotating face 24. The fixed face 22 and the rotating face 24 form the two parts of the mechanical seal that slide near each other during normal operation. During normal operation, a thin liquid film forms at the interface of the fixed face 22 and the rotating face 24. The mechanical seal also includes a spring 26, a collar 28, a first O-ring 30, and a second O-ring 32. The components and operation of a mechanical seal are well known to those with skill in the art.

FIG. 1 also shows a transducer 34, for example a PZT-5A poled to operate in the transverse mode, mounted on the back of the fixed portion 18 of the mechanical seal. The transducer 34 may be driven at 4 MHz by a function generator, to produce an ultrasonic shear wave 36 directed at the interface of the fixed face 22 and the rotating face 24. During normal operation, the ultrasonic shear wave 36 would primarily be reflected from the interface. The double arrowhead line representing the ultrasonic shear wave 36 indicates the dual operation of the transducer 34 as both a wave source and a wave sensor for the reflected ultrasonic shear wave 36.

In a non-contacting seal, when the thin liquid film breaks down the asperities in the fixed face 22 and the rotating face 24 make contact. Under these circumstances a greater portion of the ultrasonic shear wave 36 passes across the interface. A measurably lesser portion of the ultrasonic shear wave 36 is reflected back to the transducer 34. The measurably lesser portion may be shown by a change in amplitude of the reflected wave. In a partially contacting seal, there is contact during normal operation that becomes more severe when the film breaks down. In a partially contacting seal, as in a non-contacting seal, when the thin film breaks down a greater portion of the ultrasonic shear wave 36 passes across the interface and a measurably lesser portion of the ultrasonic shear wave 36 is reflected back to the transducer 34.

Also shown in FIG. 1 are an analyzer 38a and an analyzer lead 40a running between the transducer 34 and the analyzer 38a. The analyzer 38a may be any device capable of controlling the transducer 34 and analyzing the signal received from the transducer 34. The analyzer 38a may include an oscilloscope, a memory element, a personal computer, and digital signal processor. If a computer is used as an analyzer, the signal can be filtered and transformed to the frequency domain with a Fast Fourier Transform (FFT) and the peak amplitude recorded, tracked and temperature compensated. The operation of the analyzer 38a in combination with a transducer is well known in the art. Among others devices, the analyzer lead 40a may be copper wire or the analyzer lead 40a may be wireless.

The analyzer 38a of the condition monitor for an interface can be implemented in hardware, software, firmware, or a combination thereof. In the preferred embodiment(s), the analyzer is implemented in software or firmware that is stored in a memory and that is executed by a suitable instruction execution system. If implemented in hardware, as in an alternative embodiment, the analyzer can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Mounted to the rear of the transducer 34 is a thermocouple 42a for temperature correction of the transducer 34. The thermocouple 42a may be mounted anywhere as long as it is subject to the same temperature variations as the transducer 34, i.e. in thermatic connection. The thermocouple 42a is connected to the analyzer 38a by thermocouple lead 44a. The instantaneous temperature and calibration curves are used to provide the temperature correction. The calibration curves are obtained from measurements inside a temperature-controlled oven.

FIG. 2 shows a cut-away view of the machine housing of FIG. 1, a first transducer for producing a shear wave, and a second transducer for detecting the shear wave after the shear wave interacts with the interface of the mechanical seal. The machine housing and condition monitoring system as a whole is shown by reference numeral 50. Other than changes noted immediately below, FIG. 2 is identical to FIG. 1. FIG. 2 shows a first transducer 52 mounted on the back of the annular fixed portion 18 of the mechanical seal and a second transducer 54 mounted on the back of the rotating portion 20 of the mechanical seal. The first transducer 52 produces an ultrasonic shear wave 56 and the second transducer 54 detects the ultrasonic shear wave 56 after it passes through the interface of the fixed face 22 and the rotating face 24. The second transducer 54 of the condition monitor of FIG. 2 detects a measurably greater ultrasonic shear wave 56 when the liquid film in the interface breaks down and the asperities in the fixed face 22 and the rotating face 24 make contact.

Also in FIG. 2, an analyzer 38b controls first transducer 52 through one of two analyzer leads 40b and receives a signal from second transducer 54 through the second of two analyzer leads 40b. Although FIG. 2 shows the wave producing first transducer 52 mounted on the back of the annular fixed portion 18, the operation of the transducers could be reversed in which case the transducer mounted on the back of the annular fixed portion 18 would detect a wave produced by the transducer mounted on the back of the rotating portion 20.

Mounted to the rear of the first transducer 54 is a first thermocouple 42b for temperature correction of the first transducer 54. Mounted to the rear of the second transducer 54 is second thermocouple 58 for temperature correction of second transducer 54. The first thermocouple 42b is connected to the analyzer 38b by thermocouple lead 44b and the second thermocouple 58 is connected to the analyzer 38b by thermocouple lead 59.

FIG. 3 shows a cut-away view of a machine housing and a single transducer for monitoring the interface of two seals in a second type of mechanical seal. The machine housing and condition monitoring system as a whole is shown by reference numeral 50. In detail, FIG. 3 shows a machine housing 52. A seal chamber 54 is located in the machine housing 52. The seal chamber contains a fluid. A shaft 56 is also shown.

Around the shaft 56, and within the machine housing 52, is an annular fixed portion 58 of a mechanical seal. Also around the shaft 56, and within the machine housing 52, is an annular rotating portion 60 of the mechanical seal. The annular fixed portion 58 includes a front with a fixed face 62. And the annular rotating portion 60 includes a front with a rotating face 64. The fixed face 62 and the rotating face 64 form the two parts of the mechanical seal that slide near each other normal during operation. During normal operation, a thin liquid film forms at the interface of the fixed face 62 and the rotating face 64. The mechanical seal also includes a spring 66, a collar 68, a first O-ring 70, and a second O-ring 72. The components and operation of a mechanical seal are well known to those with skill in the field.

FIG. 3 also shows a transducer 74 mounted on the back of the annular fixed portion 58 of the mechanical seal. The transducer 74 produces an ultrasonic shear wave 76 directed at the interface of the fixed face 62 and the rotating face 64. During normal operation, the ultrasonic shear wave 76 is primarily reflected from the interface. The double arrowhead line representing the ultrasonic shear wave 76 indicates the dual operation of the transducer 74 as both a wave source and a wave sensor for the reflected ultrasonic shear wave 76. Also shown in FIG. 3 are an analyzer 78a and an analyzer lead 80a running between the transducer 74 and the analyzer 78a.

Mounted to the rear of the transducer 74 is a thermocouple 82a for temperature correction of the transducer 74. The thermocouple 82a is connected to the analyzer 78a by thermocouple lead 84a.

Figure 4:
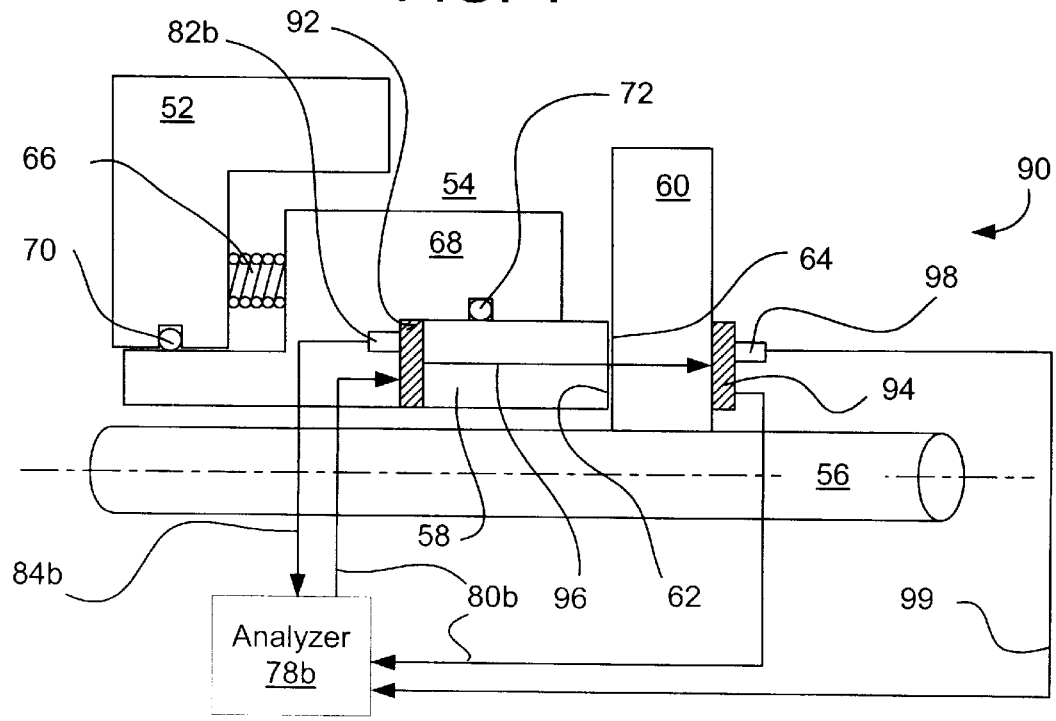
FIG. 4 is a cut-away view of a machine housing, a first transducer for producing a shear wave, and a second transducer for detecting the shear wave after the shear wave interacts with the interface of the mechanical seal of FIG. 3 and a block diagram showing an analyzer.

FIG. 4 shows a cut-away view of the machine housing of FIG. 3, a first transducer for producing a shear wave, and a second transducer for detecting the shear wave after the shear wave interacts with the interface of the second mechanical seal. The machine housing and condition monitoring system as a whole is shown by reference numeral 90. Other than changes noted immediately below, FIG. 4 is identical to FIG. 3. FIG. 4 shows a first transducer 92 mounted on the back of the annular fixed portion 58 of the mechanical seal and a second transducer 94 mounted on the back of the rotating portion 60 of the mechanical seal. The first transducer 92 produces an ultrasonic shear wave 96 and the second transducer 94 detects the ultrasonic shear wave 96 after it passes through the interface of the fixed face 62 and the rotating face 64. The second transducer 94 of the condition monitor of FIG. 4 detects a measurably greater ultrasonic shear wave 96 when the liquid film breaks down and the asperities in the fixed face 62 and the rotating face 64 make contact.

In FIG. 4, an analyzer 78b controls first transducer 92 through one of two analyzer leads 80b and receives a signal from second transducer 94 through the second of two analyzer leads 80b. Although FIG. 4 shows the wave producing first transducer 92 mounted on the back of the annular fixed portion 58, the operation of the transducers could be reversed in which case the transducer mounted on the back of the annular fixed portion 58 would detect a wave produced by the transducer mounted on the back of the rotating portion 60.

Mounted to the rear of the first transducer 92 is a first thermocouple 82b for temperature correction of the first transducer 92. Mounted to the rear of the second transducer 94 is a second thermocouple 98. The first thermocouple 82b is connected to the analyzer 78b by thermocouple lead 84b and the second thermocouple 98 is connected to the analyzer by thermocouple lead 99.

Figure 5:
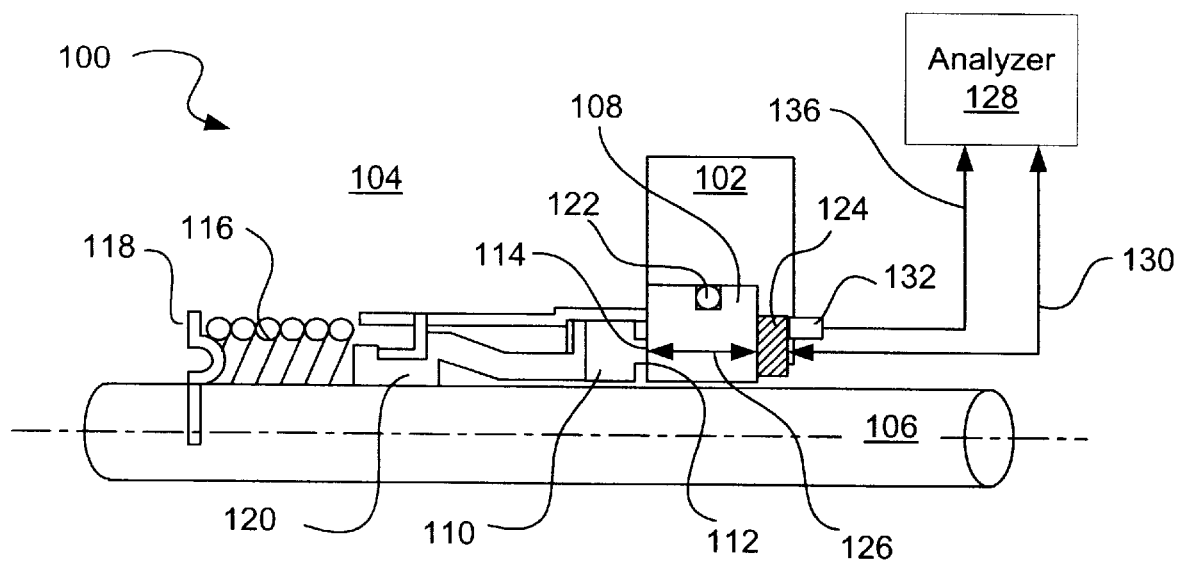
FIG. 5 is a cut-away view of a machine housing and a single transducer for monitoring the interface of two seal faces in a third type of mechanical seal and a block diagram showing an analyzer.

FIG. 5 shows a cut-away view of a machine housing and a single transducer for monitoring the interface of two seals in a third type of mechanical seal. The machine housing and condition monitoring system as a whole is shown by reference numeral 100. In detail, FIG. 5 shows a first portion of a machine housing 102. A seal chamber 104 is located in the machine housing 102. The seal chamber contains a fluid. A shaft 106 is also shown.

Around the shaft 106, and within the machine housing 102, is an annular fixed portion 108 of a mechanical seal. Also around the shaft 106, and within the machine housing 102, is an annular rotating portion 110 of the mechanical seal. The annular fixed portion 108 of the mechanical seal includes a front with a fixed face 112. And the annular rotating portion 110 of the mechanical seal includes a front with a rotating face 114. The fixed face 112 and the rotating face 114 form the two parts of the mechanical seal that slide near each other during normal operation. During normal operation, a thin liquid film forms at the interface of the fixed face 112 and the rotating face 114. The mechanical seal also includes a spring 116, a collar 118, a rubber bellows 120, and an O-ring 122.

FIG. 5 also shows a transducer 124 mounted on the back of the annular fixed portion 108 of the mechanical seal. The transducer 124 produces an ultrasonic shear wave 126 directed at the interface of the fixed face 112 and the rotating face 114. During normal operation, the ultrasonic shear wave is primarily reflected from the interface. The double arrowhead line representing the ultrasonic shear wave 126 indicates the dual operation of the transducer 124 as both a wave source and a wave sensor for the reflected ultrasonic shear wave 124.

Also shown in FIG. 5 are an analyzer 128 and an analyzer lead 130 running between the transducer 94 and the analyzer 128. Mounted to the rear of the transducer 124 is a thermocouple 132 for temperature correction of the transducer 124. The thermocouple 132 is connected to the analyzer 128 by thermocouple lead 134.

Figure 6:
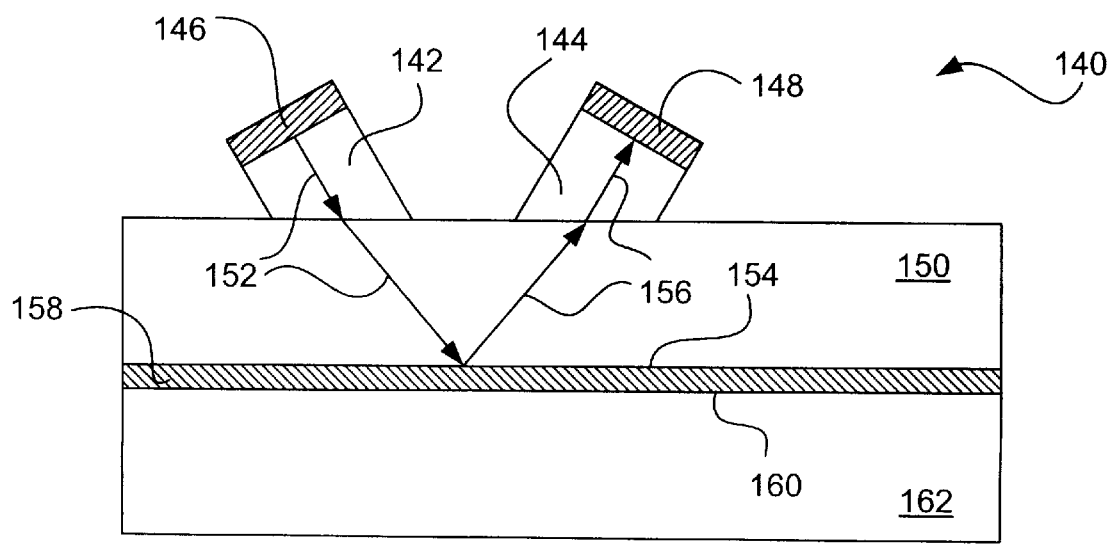
FIG. 6 is a cut-away view of an alternative arrangement for the first and second transducers in which the first and second transducers are on the same side of the interface of a mechanical seal.

FIG. 6 is a cut-away view of an alternative arrangement for a first and a second transducer in which the first and second transducers are on the same side of the interface of a mechanical seal. The alternative arrangement as a whole is shown by reference numeral 140. A first metal mount 142 and a second metal mount 144 are shown. Although metal mounts are shown in FIG. 6, the mounts may also be constructed from ceramic or other materials. A first transducer 146 and a second transducer 148 are mounted to a first surface of the first metal mount 142 and the second metal mount 144 respectively. An opposing second surface of the first metal mount 142 and an opposing surface of the second metal mount 144 are at an angle to the first surface to allow for the positioning of the first transducer 146 and the second transducer 148 at angles to the back of the stationary portion 150 of a mechanical seal. Positioning the first transducer 146 and the second transducer 148 at an angle allows the first transducer 146 to direct a shear wave 152 at an angle to the fixed face 154 of the stationary portion 150 of the mechanical seal and allows the second transducer 148 to detect the reflected shear wave 156 from the interface 158 of the fixed face 154 and the rotating face 160 of the rotating portion 162 of the mechanical seal It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed:

1. A system for monitoring an interface, comprising:
    a wave source, the wave source being capable of producing a shear wave directed at the interface, the wave source being on a first side of the interface;
    a wave sensor, the wave sensor being capable of detecting the shear wave after the shear wave interacts with the interface, the wave sensor being on a second side of the interface;
    a wave analyzer, the wave analyzer being capable of producing an output based on a comparison between the detected shear wave and predefined wave characteristics; and
    a thermocouple in thermatic connection with the wave source, wherein the analyzer is capable of correcting the output based on input from the thermocouple.

2. The system of claim 1, wherein the wave source is a transducer.

3. The system of claim 1, wherein the wave source is a piezoelectric transducer.

4. The system of claim 1, wherein the shear wave is an ultrasonic wave.

5. The system of claim 1, wherein the interface is the interface of two seal faces.

6. The system of claim 1, wherein the interface is the interface of two mechanical seal faces.

7. The system of claim 6, wherein the two mechanical seal faces are contacting.

8. The system of claim 6, wherein the two mechanical seal faces are non-contacting.

9. The system of claim 1, wherein the shear wave is an ultrasonic wave, and the interface is the interface of two mechanical seal faces.

10. The system of claim 1, wherein the wave sensor is a piezoelectric transducer.

11. The system of claim 1, wherein the wave source is capable of producing a compressive wave directed at the interface, the wave sensor is capable of detecting the compressive wave after the compressive wave interacts with the interface, the wave analyzer is capable of comparing the detected compressive wave to predefined wave characteristics, and the output contains information regarding the comparison between the detected compressive wave and the predefined wave characteristics.

12. A system for monitoring an interface, comprising:
    a wave source, the wave source being capable of producing a shear wave directed at the interface, the wave source being on a first side of the interface;
    a wave sensor, the wave sensor being capable of detecting the shear wave after the shear wave interacts with the interface, the wave sensor being on a second side of the interface;
    a wave analyzer, the wave analyzer being capable of producing an output based on a comparison between the detected shear wave and predefined wave characteristics; and
    a thermocouple in thermatic connection with the wave sensor, wherein the analyzer is capable of correcting the output based on input from the thermocouple.

13. The system of claim 12, wherein the wave source is a transducer.

14. The system of claim 12, wherein the wave source is a piezoelectric transducer.

15. The system of claim 12, wherein the shear wave is an ultrasonic wave.

16. The system of claim 12, wherein the interface is the interface of two seal faces.

17. The system of claim 12, wherein the interface is the interface of two mechanical seal faces.

18. The system of claim 12, wherein the shear wave is an ultrasonic wave, and the interface is the interface of two mechanical seal faces.

19. The system of claim 12, wherein the wave sensor is a piezoelectric transducer.

20. The system of claim 12, further including a thermocouple in thermatic connection with the wave source, wherein the analyzer is capable of correcting the output based on input from the thermocouple.

21. The system of claim 12, wherein the wave source is capable of producing a compressive wave directed at the interface, the wave sensor is capable of detecting the compressive wave after the compressive wave interacts with the interface, the wave analyzer is capable of comparing the detected compressive wave to predefined wave characteristics, and the output contains information regarding the comparison between the detected compressive wave and the predefined wave characteristics.

22. A system for monitoring an interface, comprising:
    a wave source, the wave source being capable of producing a shear wave directed at the interface, the wave source being on a first side of the interface;
    a wave sensor, the wave sensor being capable of detecting the shear wave after the shear wave interacts with the interface, the wave sensor being on a second side of the interface;
    a thermocouple, the thermocouple in thermatic connection with the wave sensor; and
    a wave analyzer, the wave analyzer being capable of producing an output based on a comparison between the detected shear wave and predefined wave characteristics, wherein the analyzer is capable of correcting the output based on input from the thermocouple.

23. The system of claim 22, wherein the wave source is a transducer.

24. The system of claim 22, wherein the wave source is a piezoelectric transducer.

25. The system of claim 22, wherein the shear wave is an ultrasonic wave.

26. The system of claim 22, wherein the interface is the interface of two mechanical seals.

27. The system of claim 26, wherein the two mechanical seal faces are contacting.

28. The system of claim 22, wherein the device is a piezoelectric transducer.

29. The system of claim 22, further including a thermocouple wherein the analyzer is capable of correcting the output based on input from the thermocouple.

30. The system of claim 29, wherein the thermocouple in thermatic connection with the wave source.

31. The system of claim 29, wherein the thermocouple in thermatic connection with the wave sensor.

32. The system of claim 22, wherein the wave source is capable of producing a compressive wave directed at the interface, the wave sensor is capable of detecting the compressive wave after the compressive wave interacts with the interface, the wave analyzer is capable of comparing the detected compressive wave to predefined wave characteristics, and the output contains information regarding the comparison between the detected compressive wave and the predefined wave characteristics.

33. A system for monitoring an interface, comprising:
  a wave source, the wave source being capable of producing a wave directed at the interface;
  a wave sensor, the wave sensor being capable of detecting the wave after the wave interacts with the interface;
  a thermocouple, the thermocouple in thermatic connection with one of a group consisting of the wave source and the wave sensor; and
  a wave analyzer, the wave analyzer being capable of producing an output based on a comparison between the detected wave and predefined wave characteristics, and the wave analyzer being capable of correcting the output based on input from the thermocouple.

34. The system of claim 33, wherein the wave source is a transducer.

35. The system of claim 33, wherein the wave source and the wave sensor are the same device.

36. The system of claim 33, wherein the wave is an ultrasonic wave.

37. The system of claim 33, wherein the interface is the interface of two seal faces.

38. The system of claim 33, wherein the wave source and the wave sensor are the same device, the shear wave is an ultrasonic wave, and the interface is the interface of two seal faces.

39. A system for monitoring an interface of two seal faces, comprising:
  a wave source, the wave source being capable of producing a shear wave directed at the interface of the two seal faces;
  a wave sensor, the wave sensor being capable of detecting the shear wave after the shear wave interacts with the interface of the two seal faces;
  a wave analyzer, the wave analyzer being capable of producing an output based on a comparison between the detected shear wave and predefined wave characteristics; and
  a thermocouple, wherein the analyzer is capable of correcting the output based on input from the thermocouple.

40. The system of claim 39, wherein the wave source is a transducer.

41. The system of claim 39, wherein the wave source is a piezoelectric transducer.

42. The system of claim 39, wherein the wave source and the wave sensor are the same device.

43. The system of claim 39, wherein the shear wave is an ultrasonic wave.

44. The system of claim 39, wherein the two seal faces are mechanical seal faces.

45. The system of claim 44, wherein the two mechanical seal faces are contacting.

46. The system of claim 44, wherein the two mechanical seal faces are non-contacting.

47. The system of claim 39, wherein the wave source is on a first side of the interface and the wave sensor is on a second side of the interface.

48. The system of claim 39, wherein the wave source and the wave sensor are the same device, the shear wave is an ultrasonic wave, and the interface is the interface of two mechanical seal faces.

49. The system of claim 48, wherein the device is a piezoelectric transducer.

50. The system of claim 39, wherein the thermocouple is in thermatic connection with the wave source.

51. The system of claim 39, wherein the thermocouple is in thermatic connection with the wave sensor.

52. The system of claim 39, wherein the wave source is capable of producing a compressive wave directed at the interface, the wave sensor is capable of detecting the compressive wave after the compressive wave interacts with the interface, the wave analyzer is capable of comparing the detected compressive wave to predefined wave characteristics, and the output contains information regarding the comparison between the detected compressive wave and the predefined wave characteristics.

* * * * *